US012048727B2

(12) United States Patent
Agnihotri et al.

(10) Patent No.: US 12,048,727 B2
(45) Date of Patent: Jul. 30, 2024

(54) SYNERGISTIC FORMULATION AGAINST ACNE AND A PROCESS FOR THE PREPARATION THEREOF

(71) Applicant: COUNCIL OF SCIENTIFIC & INDUSTRIAL RESEARCH, New Delhi (IN)

(72) Inventors: Vijai Kant Agnihotri, Palampur (IN); Bipul Kumar, Delhi (IN); Hemant Kumar Gautam, Delhi (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 521 days.

(21) Appl. No.: 17/598,277

(22) PCT Filed: Mar. 20, 2020

(86) PCT No.: PCT/IN2020/050263
§ 371 (c)(1),
(2) Date: Sep. 26, 2021

(87) PCT Pub. No.: WO2020/202176
PCT Pub. Date: Oct. 8, 2020

(65) Prior Publication Data
US 2022/0184171 A1 Jun. 16, 2022

(30) Foreign Application Priority Data
Mar. 29, 2019 (IN) .............................. 201911012430

(51) Int. Cl.
| *A61K 36/9066* | (2006.01) |
| *A61K 36/28* | (2006.01) |
| *A61K 36/282* | (2006.01) |
| *A61K 36/35* | (2006.01) |
| *A61K 36/906* | (2006.01) |
| *A61P 17/10* | (2006.01) |
| *A61P 31/02* | (2006.01) |

(52) U.S. Cl.
CPC .......... *A61K 36/9066* (2013.01); *A61K 36/28* (2013.01); *A61K 36/282* (2013.01); *A61K 36/35* (2013.01); *A61K 36/906* (2013.01); *A61P 17/10* (2018.01); *A61P 31/02* (2018.01); *A61K 2236/331* (2013.01); *A61K 2236/37* (2013.01)

(58) Field of Classification Search
CPC .. A61K 36/9066; A61K 36/28; A61K 36/282; A61K 36/35; A61K 36/906; A61K 2236/331; A61K 2236/37; A61P 17/10; A61P 31/02
See application file for complete search history.

(56) References Cited

U.S. PATENT DOCUMENTS

| 5,981,473 A | 11/1999 | Barefoot et al. |
| 7,785,638 B2 | 8/2010 | Mitra et al. |
| 2004/0185123 A1 | 9/2004 | Mazzio et al. |
| 2016/0184220 A1 | 6/2016 | Woody |

OTHER PUBLICATIONS

Consensus, I. A. A. "Epidemiology of acne." Indian J. Dermatol Venerol Leprol 2009, vol. 75, Supplement 1.
Kumar B, Pathak R et al. 2016. New insights into acne pathogenesis: Exploring the role of acne associated microbial population. Dermatologica Sinica 34: 67-73.
Jappe U T A. 2003 Pathological mechanisms of acne with special emphasis on Propionibacterium acnes and related therapy. Acta Derm Venereol 83: 241-248.
McDowell Andrew et al. 2013 "Propionibacterium acnes in human health and disease." BioMed research international.
Rathi S K. 2011 Acne vulgaris treatment: The current scenario. Indian J Dermatol 56: 7-13.
Sardana K, et al. 2106. A cross-sectional pilot study of antibiotic resistance in P. acnes strains in Indian acne patients using 16S rRNA polymerase chain reaction: A comparison among treatment modalities including antibiotics, benzoyl peroxide and isotretinoin. Indian J Dermatol 61: 45-52.
Warnke Patrick H., et al. 2009. The battle against multi-resistant strains: renaissance of antimicrobial essential oils as a promising force to fight hospital-acquired infections. Journal of Cranio-Maxillofacial Surgery 37.7: 392-397.
Groppo F. C., et al. Antimicrobial activity of garlic, tea tree oil, and chlorhexidine against oral microorganisms. International dental journal 52.6 (2002): 433-437.
Lakhdar L., et al. "Antibacterial activity of essential oils against periodontal pathogens: a qualitative systematic review." Odontostomatol Trop 35.140 (2012): 38-46.
Carvalhinho, Sara, et al. "Susceptibilities of Candida albicans mouth isolates to antifungal agents, essentials oils and mouth rinses." Mycopathologia 174.1 (2012): 69-76.
Karbach J., et al. "Antimicrobial effect of Australian antibacterial essential oils as alternative to common antiseptic solutions against clinically relevant oral pathogens." Clin Lab 61.1-2 (2015): 61-8.
Devi K. Pandima et al. "Eugenol (an essential oil of clove) acts as an antibacterial agent against *Salmonella typhi* by disrupting the cellular membrane." Journal of ethnopharmacology 130.1 (2010): 107-115.
Kumar Bipul et al. "Evaluation of antimicrobial efficacy of quaternized poly [bis (2-chloroethyl) ether-alt-1, 3-bis [3-(dimethylamino) propyl] urea] against targeted pathogenic and multi-drug-resistant bacteria." Journal of Bioactive and Compatible Polymers 31.5 (2016): 467-480.

(Continued)

*Primary Examiner* — Trevor Love
(74) *Attorney, Agent, or Firm* — Blank Rome LLP

(57) ABSTRACT

The present invention relates to a synergistic formulation comprising the essential oils of plants from western Himalayas, which have versatile medicinal properties. The present invention also relates to a process for development of synergistic value added anti-acnes products using the essential oils from these plants of western Himalayas. The developed synergistic formulation is useful in inhibiting different *P. acnes* strains thereby exhibiting antibacterial activity.

6 Claims, No Drawings

(56) References Cited

OTHER PUBLICATIONS

Kang Jong-Seok et al. "Antibacterial, whitening, and anti-wrinkling effects of essential oil from Curcuma aromatica leaves." Der Pharma Chemica, 2016, 8(18):95-99. p. 97.
Taget (*Tagetes minuta*), webpage, Jan. 24, 2016. www.naturalbynature.co.uk/taget.
Kapur Kachri essential oil (*Hedycchium spicatum*), webpage, Feb. 26, 2019 https://www.rkaroma.com/kapur-kachri-essential-oil-brhedychium-spicatum.
Valeriana jatamansi—Jones, webpage, Jul. 15, 2011 https://pfaf.org/user/Plant.aspx?LatinName=Valeriana+jatamansi.
Curcuma aromatica Salisb., Jul. 27, 2017 https://indiabiodiversity.org/species/show/229360.
Search Report dated Aug. 28, 2020, for corresponding International Application No. PCT/IN2020/050263.

SYNERGISTIC FORMULATION AGAINST ACNE AND A PROCESS FOR THE PREPARATION THEREOF

CROSS REFERENCE TO RELATED APPLICATIONS

This application is a national phase of PCT application No. PCT/IN2020/050263, filed Mar. 20, 2020, which claims priority to IN patent application No. 201911012430, filed Mar. 29, 2019 which is incorporated herein by reference thereto.

FIELD OF THE INVENTION

The present invention relates to a synergistic formulation comprising essential oils and a process for the preparation thereof. The prepared formulation is useful in development of value added anti-acne product. The present invention further relates to development of a composition exhibiting specific anti-acne activity using essential oils of plants from western Himalayan region such as *Tagetes minuta*, *Hedychium spicatum*, *Curcuma aromatica*, *Valeriana jatamansi*, *Dracocephalum heterophyllum* and *Artemisia maritima*. The synergistic formulation of essential oil developed in the present invention finds utility in perfumery, fragrance, pharmaceutical, skin care, food, agrochemicals, in other household or agricultural applications and the like.

BACKGROUND OF THE INVENTION AND DESCRIPTION OF PRIOR ART

Acne or Acne vulgaris is a common skin disease of pilosebaceous unit, which afflicts, approximately 90% of adolescent population in westernized countries (Barefoot S F, Ratnam P. 1999 Composition and method for treating acne. U.S. Pat. No. 5,981,473A). In India 38.13% of girls and 50.6% of boys in age group 12-17 years are afflicted with this disease (Epidemiology of acne 2009 *Indian J Dermatol Venereol Leprol*. 75). Acne, a prevalent disorder of skin, is found to increase the incidence of suicidal ideation in the acne patient (7.1%) (Kumar B, Pathak R, Mary P B, Jha D, Sardana K, Gautam H K. 2016 New insights into acne pathogenesis: Exploring the role of acne associated microbial population. *Dermatologica Sinica* 34: 67-73).

Multiple forms of acne occur according to the American Academy of Dermatology. The most common is formation of comedones such as blackheads, whiteheads and pimples, to more severe condition of acne that includes bacterial infection in papules, nodules and cyst (Woody S T. 2016 Method for the prevention and treatment of acne. US 2016/0184220A1). The part of body that are mainly affected by acne are face, chest, neck, shoulders and upper back because of the presence of high number of sebaceous gland (Barefoot S F, Ratnam P. 1999 Composition and method for treating acne. U.S. Pat. No. 5,981,473A). There are many factors being involved in formation of acne lesions like bacterial colonization of the pilosebaceous ducts, sebum production, inflammation and ductal cornification (Jappe U T A. 2003 Pathological mechanisms of acne with special emphasis on *Propionibacterium acnes* and related therapy. *Acta Derm Venereol* 83: 241-248).

The main inducer for this multifactorial disease is microbial fluctuation of common resident microbes on skin with each microbe possessing their own purpose and style in protecting the human body (Kumar B, Pathak R, Mary P B, Jha D, Sardana K, Gautam H K. 2016 New insights into acne pathogenesis: Exploring the role of acne associated microbial population. *Dermatologica Sinica* 34: 67-73).

*Propionibacterium acnes* (*P. acnes*) is a Gram-positive, anaerobic bacterium that plays a major role in the pathogenesis of acne (McDowell A, Patrick S, Eishi Y, Lambert P, Eady A. 2013 *Propionibacterium acnes* in human health and disease. *BioMed Research International* 2013: 3p). The proliferation of *P. acnes* in an environment is created by a mixture of excessive sebum and follicular cells and produce chemotactic factors and pro-inflammatory mediators that may lead to inflammation (Mitra S K, Saxena E, Babu U V. 2010 Herbal acne control composition, method of manufacturing the same and use thereof. U.S. Pat. No. 7,785,638B2).

There are many different treatments that include topical retinoids, topical or synthetic antibiotics or hormonal therapies or oral isotretinoin, mostly available for acne, depends on the type of clinical lesions. Benzyl peroxide or topical antibiotics like erythromycin, clindamycin or oral isotretinoin or combination of all these mediators are available for mild to moderate inflammatory acne. But now days, some of these treatments are producing adverse side effects (Rathi S K. 2011 Acne vulgaris treatment: The current scenario. *Indian J Dermatol* 56: 7-13).

Antibiotics like clindamycin, minocycline, tetracycline, doxycycline and erythromycin are frequently used by acne patients. However, the administration of these drugs brings a lot of side effects like abdominal cramps, black tongue, nausea, depression, fatigue and dryness of skin (Barefoot S F, Ratnam P. 1999 Composition and method for treating acne. U.S. Pat. No. 5,981,473A).

Across the world, the high prevalence of antibiotic resistance is a problem in acne patients due to regional prescription practices, patient compliance and genomic variability in *P. acnes*. Our lab study revealed high resistance of antibiotics likes azithromycin (100%), erythromycin (98%), clindamycin (90.4%), doxycycline (444.2%) and tetracycline (30.8%), whereas low resistance was observed to minocycline (1.9%) and levofloxacin (9.6%) in the Indian population (Sardana K, Gupta T, Kumar B, Gautam H K, Garg V K. 2106 A cross-sectional pilot study of antibiotic resistance in *P. acnes* strains in Indian acne patients using 16S rRNA polymerase chain reaction: A comparison among treatment modalities including antibiotics, benzoyl peroxide and isotretinoin. *Indian J Dermatol* 61: 45-52).

Antimicrobial resistance (AR) poses a serious threat to mankind across the world. Treatments using current line of therapeutics available in clinical practice have shown several cases of emerging AR. The rate of antibiotic discovery is exceptionally low as compared to increasing antibiotic resistance. The situation is alarming and it is strategic threat to the entire world. One approach to manage the antibiotic resistance is to exploit traditional knowledge and to bring their antibiotic potential on discovery platform.

Essential oils are well known for their versatile medicinal properties. An essential oil is a concentrated, hydrophobic liquid containing volatile aroma compounds from plants. Essential oils are also known as volatile oils, ethereal oils or aetherolea, or simply as the "oil of" the plant from which they were extracted. Various essential oils have been used medicinally at different periods in history. Medical application proposed for medicinal oils range from skin treatments to remedies for cancer, and often are based on nothing better than historical accounts of use of essential oils for these purposes. As per literature survey, the essential oils contain very good antibacterial activity (French System of Medicine). The emergence of resistant strains with consistent usage of antimicrobials has led to use of essential oils against micro-organisms in vitro and in vivo (Warnke P H, Becker S T, Podschun R, et al. J Craniomaxillofac Surg 2009; 37:392-397; Groppo F C, Ramacciato J C, Simoes R P, Florio F M, Sartoratto A. Int. Dent J 2002; 52:433-437). Worldwide, they are frequently used in dermatology, aromatherapy and cosmetology to treat a variety of conditions such as acne, dandruff, hair lice, recurrent herpes labialis and oropharyngeal candidiasis. Till date several studies have analyzed the effect of pure essential oils and antiseptics (Lakhdar L, Hmamouchi M, Rida S, Ennibi O. Odontostomatol Trop 2012; 35:38-46.) to bacteria and yeasts (Carvalhinho S, Costa A M, Coelho A C, Martins E, Sampaio A. Mycopathologia 2012; 174:69-76). Most of the studies have revealed that using essential oils as a mouth rinse, the total amount of oral bacteria as well as mutants streptococci can be reduced (Karbach J, Ebenezer S, Warnke P H, Behrens E., Al-Nawas B. Clin Lab 2015; 61:61-68). The exact compositions of essential oils depend on the species of plant of origin. They include hydrocarbons, alcohols, esters, ethers, ketones and aldehydes. They are hydrophobic in nature. This character enables them to partition the lipid of the bacterial cell membrane and mitochondria, making them permeable and eventually disturbing the cell structure. It leads to leaching out of critical molecules and ions, which results in death of bacterial cell (Devi K P, Nisha S A, Sakthivel R, Pandian S K. J. Ethnopharmacology, 2010; 130:107-15).

Thus, keeping in view the drawbacks of the hitherto reported prior art, the present invention attempts to address the problems of multi drug resistance of *P. acnes* by excessive use of antibiotics.

OBJECTIVES OF THE INVENTION

The main objective of the present invention is to provide a synergistic formulation comprising essential oils of plants from western Himalayas.

Another objective of the present invention is to provide an easy and convenient method for transformation of the essential oils of plants from western Himalayas into anti-acne products.

Yet another objective of the present invention is to provide a methodology for preparation of anti-acne formulations from essential oils.

Still another objective of the present invention is to prepare different biologically active products from essential oils of plants from western Himalayas.

SUMMARY OF THE INVENTION

Accordingly, the present invention provides a synergistic formulation comprising essential oils of plants from western Himalaya mixed in the different proportions.

In an embodiment of the present invention, there is provided a synergistic formulation comprising essential oils of *T. minuta, H. spicatum, C. aromatica, A. maritime, D. heterophyllum* and *V. jatamansi* in different proportions ranging from 1 to 60% w/v.

In another embodiment of the present invention, there is provided a synergistic formulation, wherein the active components of the essential oils comprise 1,8-cineol, patchouli alcohol, ocimene, dihydrotagetone, camphor, citronellol, isoborneol and borneol.

In yet another embodiment of the present invention, there is provided a process for preparation of the formulation comprising the steps of:

(i) providing essential oils of plants from western Himalayas;
(ii) mixing the essential oils of plants provided in step (i) in different ratios to obtain a mixture;
(iii) mixing the mixture as obtained in step (ii) using a magnetic stirrer at room temperature in the range of 15° C. to 25° C. for 1-3 hours;
(iv) diluting the mixture as obtained in step (iii) by adding a diluting agent in the ratio of essential oil:diluting agent as 1:0-1:10000 and mixing for 1-2 hours at room temperature; and
(v) applying the mixture obtained in step (iv) on different *P. acne* strains for assessing the antibacterial activity.

In yet another embodiment of the present invention, the essential oil is obtained from aerial parts of *T. minuta, A. maritime, D. heterophyllum* and rhizomes of *V. jatamansi, H. spicatum* and *C. aromatica* as a whole or in crushed form.

In still another embodiment of the present invention, the essential oils of *T. minuta, A. maritima, H. spicatum, C. aromatic, D. heterophyllum* and *V. jatamansi* were extracted by steam distillation or hydro-distillation or combination thereof for a period in the range of 5 min to 72 hrs.

In yet another embodiment of the present invention, the diluting agent is selected from the group consisting of an organic solvent and an inorganic solvent or combination thereof.

In still another embodiment of the present invention, the organic solvent is selected from the group of hydrocarbons, alcohols, ethers, and esters.

In still another embodiment of the present invention, the final formulation contains preservatives, selected from the group consisting of benzoic acid, butylated hydroxy anisole (BHA), sodium benzoate, and parabens. If desired, drying agents may also be added to the formulation.

In yet another embodiment of the present invention, the essential oils can be obtained from plants growing in other geographical area.

In still another embodiment of the present invention, the final formulation is active against different microbes.

In yet another embodiment of the present invention, the final formulation is in a concentrated form which is free from any solvent residue.

In still another embodiment of the present invention, the final formulation is freely soluble in a non-polar or a medium polar solvent, and can also be mixed with emulsions, gels, lotions or a combination thereof.

In yet another embodiment of the present invention, the formulation is a synergistic formulation comprising essential oils of *T. minuta, A. maritima, H. spicatum, C. aromatic, D. heterophyllum* and *V. jatamansi* which can also be useful in perfumery, fragrance, cosmetics, pharmaceutical, food, agrochemical and other household or agricultural applications either in concentrated form or at different dilutions.

In still another embodiment of the present invention, the commercial use of formulation can be done in flavor, perfumery, food, pharmaceutical and allied industries for aroma, medicine and agrochemical products.

In yet another embodiment of the present invention, the development of skin care products is done by mixing the formulation in a non-polar solvent, or polar solvent or by partitioning through crystallization, fractionation or by partitioning between polar and non-polar solvent or derivatization for development of products.

An embodiment of the present invention provides a synergistic formulation comprising the essential oils of:
(a) *Valeriana jatamansi;*
(b) *Tagetes minuta;*

(c) *Curcuma aromatica;*
(d) *Artemisia maritime;* and
(e) *Hedychium spicatum;*
wherein the ratio between (a):(b):(c):(d):(e) ranges from 1 to 20:1 to 20:1 to 5:1 to 5:1 to 20.

In yet another embodiment of the present invention, there is provided a synergistic formulation, wherein said formulation comprises the essential oils of *Valeriana jatamansi: Tagetes minuta:Artemisia maritime:Hedychium spicatum* in the ratio 10:5:5:20.

In still another embodiment of the present invention, there is provided a formulation, wherein said formulation comprises the essential oils of *Valeriana jatamansi:Tagetes minuta:Curcuma aromatica:Hedychium spicatum* in the ratio 20:10:5:10.

In yet another embodiment of the present invention, there is provided a synergistic formulation useful for treatment of Acne vulgaris.

In still another embodiment of the present invention, there is provided a synergistic formulation, wherein said formulation can be diluted in the range of 0.0001 to 100% prior to application.

Another embodiment of the present invention provides a process for the preparation of the formulation, said process comprising:
[a] mixing essential oils of *Valeriana jatamansi, Tagetes minuta, Curcuma aromatic, Artemisia maritime,* and *Hedychium spicatum* to obtain a mixture; and
[b] homogenizing the mixture obtained in step [a] at temperature in the range of 15 to 25° C. for 1 to 3 hours to obtain the formulation;
[c] optionally, diluting the formulation as obtained in step [b] by adding a diluting agent upto 10000 times prior to use.

In still another embodiment of the present invention, there is provided a process for the preparation of the formulation, wherein the essential oils are obtained from the aerial parts or from rhizomes or combination of both of aromatic crops selected from *Valeriana jatamansi, Tagetes minuta, Curcuma aromatica, Artemisia maritime,* and *Hedychium spicatum.*

In yet another embodiment of the present invention, there is provided a process for the preparation of the formulation, wherein the essential oils are extracted using the method selected from the group consisting of solvent distillation, steam distillation, hydro distillation, hydro-steam distillation for a period in the range of 5 minutes to 96 hours.

In still another embodiment of the present invention, there is provided a process for the preparation of the formulation, wherein the diluting agent is selected from the group consisting of a non-polar solvent, a medium polar solvent, an organic solvent, an inorganic solvent, an emulsion, a commercial cream, a gel, a lotion or combination thereof.

In yet another embodiment of the present invention, there is provided a process for the preparation of the formulation, wherein the non-polar solvent is selected from the group consisting of short-, mid- and long-chain hydrocarbons, fats, ethers and other solvents with dielectric constant less than 15.

In another embodiment of the present invention, there is provided a process for the preparation of the formulation, wherein the medium polar solvent is selected from the group consisting of short-, mid- and long-chain hydrocarbons, fats, ethers with one oxygen group and other solvents with dielectric constant is in between 15-50.

In still another embodiment of the present invention, there is provided a process for the preparation of the formulation, wherein the organic solvent is selected from the group consisting of hydrocarbons and other carbon based chemicals.

In yet another embodiment of the present invention, there is provided a process for the preparation of the formulation, wherein the inorganic solvent is selected from the group consisting of except carbon based chemicals such as water, ammonia, and carbon dioxide.

In another embodiment of the present invention, there is provided a process for the preparation of the formulation, wherein the emulsion is selected from the group consisting of mixture of two or more immiscible liquids.

In still another embodiment of the present invention, there is provided a process for the preparation of the formulation, wherein the gel is selected from the group consisting of solids dispersed in liquid medium so that can form solids with the range of properties (hard and tough to weak and soft).

In yet another embodiment of the present invention, there is provided a process for the preparation of the formulation, wherein the lotion is selected from the group consisting of range of aqueous to alcoholic liquids containing insoluble materials.

DETAILS OF BIOLOGICAL RESOURCES USED IN THE INVENTION

The biological resources used for the purposes of the present invention were plants collected from wild or from the CSIR-IHBT [CSIR-Institute of Himalayan Bioresource Technology] farm, Chandpur, Kangra, Himachal Pradesh, India. The complete details in this regard are provided in the following tables: Table 1 and Table 2.

TABLE 1

| Sl. No. | Accessed (Biological Resources OR Associated Knowledge OR Both) | Nature of biological resources (Plant OR Animal OR Microorganism) | Common name | Scientific name | Part of biological resources |
|---|---|---|---|---|---|
| 1. | Biological Resources | Plant | Wild Marigold | *Tagetes minuta* [TM] | Aerial Parts along with flowers |
| 2. | Biological Resources | Plant | Kapur Kachri | *Hedychium spicatum* [HS] | Rhizomes |
| 3. | Biological Resources | Plant | Wild Turmeric | *Curcuma aromatic* [CA] | Rhizomes |
| 4. | Biological Resources | Plant | Mushkbala | *Valeriana jatamansi* [VJ] | Rhizomes |

TABLE 1-continued

| Sl. No. | Accessed (Biological Resources OR Associated Knowledge OR Both) | Nature of biological resources (Plant OR Animal OR Microorganism) | Common name | Scientific name | Part of biological resources |
|---|---|---|---|---|---|
| 5. | Biological Resources | Plant | Thimsingli | *Dracocephalum heterophyllum* [DH] | Aerial Part |
| 6. | Biological Resources | Plant | Sea wormwood | *Artemisia maritime* [AM] | Aerial Part such as leaves |

TABLE 2

| Sl.No. | Name of the biological resource | Source of access (Wild/ Cultivated/ Market/ Trader/ Repository/ Institution/ Others) | Village/ Panchayat | Town/Taluk | District | State |
|---|---|---|---|---|---|---|
| 1. | *Tagetes minuta* | cultivated | CSIR-IHBT farm, Chandpur | Palampur | Kangra | HP |
| 2. | *Hedychium spicatum* | cultivated | CSIR-IHBT farm, Chandpur | Palampur | Kangra | HP |
| 3. | *Curcuma aromatica* | cultivated | CSIR-IHBT farm, Chandpur | Palampur | Kangra | HP |
| 4. | *Valeriana jatamansi* | cultivated | CSIR-IHBT farm, Chandpur | Palampur | Kangra | HP |
| 5. | *Dracocephalum heterophyllum* | wild | Kaza | Kaza | Lahaul-Spiti | HP |
| 6. | *Artemisia maritima* | wild | Keylong | Kaza | Keylong | HP |

DETAILED DESCRIPTION OF THE INVENTION

The present invention provides a synergistic formulation comprising essential oils of various plants from the Western Himalayas useful against acne. and the present invention also provides a process for the development of anti-acne products by using such synergistic formulation. The essential oils are obtained from the plants *Tagetes minuta, Hedychium spicatum, Curcuma aromatic, Valeriana jatamansi, Dracocephalum heterophyllum* and *Artemisia maritime*.

The process involved in the development of the claimed synergistic formulation comprises selection of different quality standardized essential oils from plants of western Himalaya and mixing them in different proportions with the help of a magnetic stirrer or by shaking manually or by mechanical shaker for two to three hours at room temperature. Then, the prepared synergistic formulation is optionally diluted with diluting agent selected from the group consisting of a non-polar solvent, a medium polar solvent, an organic solvent, an inorganic solvent, an emulsion, a commercial cream, a gel, a lotion or combination thereof along with different preservatives but not limited to binder, diluents, surfactants, perfumes and preservatives as a carrier or otherwise. The prepared mixture is further homogenized by using different devices suitable for homogenization.

The disclosed synergistic formulation is effectively useful for skin related problems, particularly for acne control. The formulation can be used for protection from pimples, blackheads, whiteheads, nodules, pustules, white heads and other skin related problems. The used essential oils and the synergistic formulation of the present invention were screened to characterize their therapeutic efficacy against the selected human *P. acnes* strains.

The essential oil of *T. minuta* is standardized against dihydrotagetone by Gas Liquid Chromatography (GLC). Similarly oils of *H. spicatum, A. maritima, V. jatamansi, D. heterophyllum* and *C. aromatica* were standardized against their phyto-chemical marker 1,8-cineol, camphor, patchouli alcohol, citronellol and borneol, respectively. All the oils were standardized for their biological activity against *P. acnes* strains isolated from skin acne lesions of Indian population. The present invention involves the selection and extraction of the essential oils by subjecting the parts of the plant to solvent extraction/hydro distillation/steam distillation or other method to isolate their active ingredients/ extracts. The bioassay guided fractionation of the extracts was done to develop a synergistic formulation comprising essential oils of *T. minuta, H. spicatum, C. aromatica, A. maritime, D. heterophyllum* and *V. jatamansi* to yield a safe cosmeceutical composition for the treatment and control of acne and skin related problems, especially in human beings.

Bacterial Strains and Culturing Conditions

In this study, pathogenic microorganisms, *Propionibacterium acnes* HKG 300 (KY674888), *Propionibacterium acnes* HKG 304 (KY674892), *Propionibacterium acnes* HKG 277 (KY674865), *Propionibacterium acnes* HKG 315 (KY674903), *Propionibacterium acnes* HKG 306

(KY674894), Propionibacterium acnes HKG 309 (KY674897), Propionibacterium acnes HKG 314 (KY674902) were isolated at CSIR-IGIB [Institute of Genomics and Integrative Biology], Mathura Road, New Delhi from human skin acne lesions and used in the examples.

Propionibacterium acnes strains were individually inoculated in 1.0 ml of Brain Heart Infusion (BHI) broth (Himedia Laboratories Pvt. Ltd, India) followed by incubation in an anaerobic chamber to maintain the anaerobic environment under an atmosphere of 80% $N_2$, 10% $CO_2$, and 10% $H_2$ at 37° C. The grown culture was further diluted in BHI broth to prepare a bacterial stock solution of concentration ~$10^5$ cfu/ml.

Minimum Inhibitory Concentration (MIC)

The Micro-broth dilution method was used in 96-well microtitre plates (Corning Technologies India Pvt. Ltd.) to obtain the MIC values of different essential oils and the synergistic formulation against various Propionibacterium acnes strains (Kumar B, Mathur A, Pathak R, Sardana K, Gautam H K, Kumar P. 2016 Evaluation of antimicrobial efficacy of quaternized poly[bis(2-chloroethyl) ether-alt-1, 3-bis [3-(dimethylamino)propyl]urea] against targeted pathogenic and multi-drug-resistant bacteria. *J Bioact Compat Polym* 31: 467-480). To carry out the experiment, stock solution of essential oils and the synergistic formulation were prepared and diluted in the range of 0.001-0.5 mg/ml. *P. acnes* cultures along with appropriate amounts of essential oils were added in Corning® 96-well plates. Essential oils solutions were tested against pathogenic bacteria from higher to lower concentrations. Subsequently, absorbance in each well was measured at 600 nm in Tecan™ 96-well plate reader and incubated at 37° C. in anaerobic condition. The minimal concentration, at which microbial survival was not noticed, was considered as minimum inhibitory concentrations (MIC). On the basis of optical density ($OD_{600\,nm}$), the survival percentage of microbes was determined. The relative survival percentage of each microbe was used to calculate the MIC, which was determined using the following formula:

Relative survival %=[OD@600 nm of treated cells/ OD@600 nm of nontreated cells (control)]×100

Levofloxacin was used as a positive control and culture medium without *P. acnes* culture and 5% aqueous DMSO with *P. acnes* culture was used as a negative control. The experiment was performed in triplicates. Standard deviation was analysed using the Microsoft Office Excel 2007.

EXAMPLES

The following examples are given by way of illustration only and therefore should not be construed to limit the scope of the present invention in any manner.

Example 1

The pathogenic microorganisms, Propionibacterium acnes HKG 300 (KY674888), Propionibacterium acnes HKG 304 (KY674892), Propionibacterium acnes HKG 277 (KY674865), Propionibacterium acnes HKG 315 (KY674903), Propionibacterium acnes HKG 306 (KY674894), Propionibacterium acnes HKG 309 (KY674897), Propionibacterium acnes HKG 314 (KY674902) were isolated at CSIR-IGIB [Institute of Genomics and Integrative Biology], Mathura Road, New Delhi from human skin acne lesions and used, as the test organisms. The test compounds are essential oils extracted from *V. jatamansi* (VJ), *A. maritima* (AM), *D. heterophyllum* (DH), *T. minuta* (TM) and *H. spicatum* (HS), respectively. The essential oils were dissolved in DMSO (5 mg/ml) and further diluted in autoclaved Milli Q water to make the working stock solution. All experiments were performed in triplicate. The results are shown in Table 3.

TABLE 3

Minimum Inhibitory Concentration (MIC) (mg/ml) of essential oil of various plants

| Samples | KY674888 | KY674892 | KY674865 | KY674903 | KY674894 | KY674897 | KY674902 |
|---|---|---|---|---|---|---|---|
| VJ | 0.25 ± 0.04 | 0.25 ± 0.04 | 0.25 ± 0.04 | 0.31 ± 0.062 | 0.2 ± 0.058 | 0.25 ± 0.04 | 0.25 ± 0.11 |
| AM | 0.35 ± 0.07 | 0.43 ± 0.047 | 0.43 ± 0.047 | 0.45 ± 0.04 | 0.35 ± 0.07 | 0.31 ± 0.062 | 0.36 ± 0.047 |
| DH | >0.5 ± 0.00* | >0.5 ± 0.00* | >0.5 ± 0.00* | >0.5 ± 0.00* | 0.4 ± 0.081 | 0.4 ± 0.081 | 0.43 ± 0.047 |
| TM | >0.5 ± 0.00* | >0.5 ± 0.00* | >0.5 ± 0.00* | >0.5 ± 0.00* | >0.5 ± 0.00* | >0.5 ± 0.00* | >0.5 ± 0.00* |
| CA | 0.35 ± 0.07 | 0.43 ± 0.047 | 0.2 ± 0.058 | 0.43 ± 0.047 | 0.25 ± 0.04 | 0.43 ± 0.047 | 0.43 ± 0.047 |
| HS | 0.30 ± 0.12 | 0.2 ± 0.058 | 0.19 ± 0.05 | 0.25 ± 0.04 | 0.2 ± 0.058 | 0.2 ± 0.00 | 0.21 ± 0.023 |

*0.5 mg/ml was the highest concentration tested.

Example 2

This example used isolated *Propionibacterium acnes* strains KY674888, KY674892, KY674865, KY674903, KY674894, KY674897, and KY674902 from skin acne lesions as the test organisms. The details of *P. acnes* and essential oils are as described above. The test synergistic formulation 55A, 55D and 55E were obtained by mixing the essential oils from VJ, AM, TM, CA and HS at different ratios: wherein The formulation 55A comprises the essential oils of VJ:TM:CA:AM:HS in the ratio of 1:1:1:1:1;

The formulation 55D comprises the essential oils of VJ:TM:CA:AM:HS in the ratio of 10:20:0:0:5 and The formulation 55E comprises the essential oils of VJ:TM:CA:AM:HS in the ratio of 0:1:1:1:1.

The synergistic formulations were dissolved in DMSO (5 mg/ml) and further diluted in autoclaved Milli Q water to make the working stock solutions. All experiments were performed in triplicate. The results are shown in Table 4.

TABLE 4

Minimum Inhibitory Concentration (MIC) (mg/ml) of synergistic formulations prepared in Example 2

| Samples | KY674888 | KY674892 | KY674865 | KY674903 | KY674894 | KY674897 | KY674902 |
|---|---|---|---|---|---|---|---|
| 55A | 0.2 ± 0.058 | 0.30 ± 0.081 | 0.125 ± 0.056 | 0.25 ± 0.04 | 0.21 ± 0.023 | 0.23 ± 0.047 | 0.4 ± 0.00 |
| 55D | 0.26 ± 0.023 | 0.26 ± 0.023 | 0.083 ± 0.02 | 0.4 ± 0.08 | 0.21 ± 0.023 | 0.26 ± 0.023 | 0.4 ± 0.00 |
| 55E | 0.25 ± 0.04 | 0.30 ± 0.07 | 0.166 ± 0.05 | 0.36 ± 0.047 | 0.25 ± 0.11 | 0.43 ± 0.047 | 0.4 ± 0.00 |

Example 3

This example used isolated *Propionibacterium acnes* strains KY674888, KY674892, KY674865, KY674903, KY674894, KY674897, and KY674902 from skin acne lesions as the test organisms. The details of *P. acnes* and essential oils are as described above. The test synergistic formulation 55B and 55C were obtained by mixing VJ, AM, TM, CA and HS essential oils at different ratios, wherein The formulation 55B comprises the essential oils of VJ:TM:CA:AM:HS in the ratio of 10:5:0:5:20 and The formulation 55C comprises the essential oils of VJ:TM:CA:AM:HS in the ratio of 20:10:5:0:10.

The synergistic formulation were dissolved in DMSO (5 mg/ml) and further diluted in autoclaved Milli Q water to make the working stock solution. All experiments were performed in triplicate. The results are shown in Table 5.

TABLE 5

Minimum Inhibitory Concentration (MIC) (mg/ml) of synergistic formulations prepared in Example 3

| Samples | KY674888 | KY674892 | KY674865 | KY674903 | KY674894 | KY674897 | KY674902 |
|---|---|---|---|---|---|---|---|
| 55B | 0.26 ± 0.023 | 0.21 ± 0.023 | 0.125 ± 0.056 | 0.2 ± 0.058 | 0.2 ± 0.058 | 0.25 ± 0.00 | 0.25 ± 0.04 |
| 55C | 0.25 ± 0.11 | 0.21 ± 0.023 | 0.125 ± 0.08 | 0.26 ± 0.023 | 0.125 ± 0.08 | 0.19 ± 0.05 | 0.31 ± 0.06 |

From the results obtained for examples 2 and 3, it was observed that the Formulations 55B and 55C exhibited best results in terms of anti-bacterial activity.

Example 4

GC-MS Analyses and Identification

The essential oils of each plant were analyzed with the help of GC/MS analyses. GC/MS analyses were conducted using a Shimadzu QP 2010 using a DB-5 (J&W Scientific, Folsom, USA) capillary column (30 m×0.25 mm i.d.; 0.25 μm thickness). Column temperature, 60° C. (3 minutes) to 240° C. (5 minutes) at 3° C./min. "Injector temperature, 250° C."; "Interface temperature, 250° C."; acquisition mass range, 800-50 amu; Detector Gain, 0.90 KV. Helium was used as carrier gas, 69.3 kPa (39.2 cm/s). Peak identification was accomplished by comparison of their mass spectral fragmentation pattern with those of reported in the literature (Adams, 1995) or by comparing with NIST library search.

GC Analyses (Quantitative Analysis)

The analysis of each essential oil was carried out by GC on Shimadzu GC-2010 equipped with a DB-5 (J&W Scientific, Folsom, USA) fusedsilica capillary column (30 m×0.25 mm i.d.; 0.25 μm film thickness). Column temperature, 90° C. (2 minutes) to 220° C. (5 minutes) with programming at 7° C./min. "Injector temperature, 240° C."; "detector temperature, 260° C."; injection mode, split. Carrier gas was helium at column flow rate of 1.05 ml/min (100 kPa). Retention indices (RI) of the sample components and authentic compounds were determined on the basis of homologous n-alkane hydrocarbons under the same conditions. The quantitative composition was obtained by peak area normalization and the response factor for each component was considered to equal 1. The results obtained in provided in Table 6.

TABLE 6

Chemical composition of essential oil from each plant.

| Constituents | VJ | AM | DH | TM | CA | HS |
|---|---|---|---|---|---|---|
| Camphor | — | — | — | — | 25.2 | — |
| Ocimene | — | — | — | 28.5 | — | — |
| Borneol | — | 6.2 | — | — | 3.7 | — |
| Isoborneol | — | — | — | — | 8.0 | — |
| Dihydrotagetone | — | — | — | 22.9 | — | — |
| Patchouli alcohol | 42.3 | — | — | — | — | — |
| Eucalyptol | — | 33.4 | — | — | — | 65.0 |
| Citronellol | — | — | 75.2 | — | — | — |

ADVANTAGES OF THE INVENTION

Anti-acnes activity obtained because of the synergy of the essential oils.

Cost effective process for development of anti-acnes product from naturally occurring essential oils.

The process provides anti-acnes product that can be produced easily by pharmaceutical industries.

Synergistic formulation has better fragrance compared to the starting materials and the new value added product can be used as a cure of acne as well as in cosmetics, fine fragrances, shampoos, toilet soaps and other toiletries.

The synergistic formulation was developed by utilizing essential oils of local plants growing in Himachal Pradesh and hence will increase the market demand of the oils. The invention will thus enhance the value of these essential oils.

*T. minuta, H. spicatum, V. jatamansi, A. maritime, D. heterophyllum* and *C. aromatica* grow abundantly in Himachal Pradesh and thus the present invention would provide an excellent opportunity to generate employment for plant collectors and also an opportunity for local people to cultivate these plants as an alternate cash crop for fulfillment of the market demand.

We claim:

1. A process for the preparation of a formulation, said process comprising:
    [a] mixing essential oils of *Valeriana jatamansi, Tagetes minuta, Curcuma aromatic, Artemisia maritime*, and *Hedychium spicatum* to obtain a mixture, wherein the ratio of *Valeriana jatamansi:Tagetes minuta:Curcuma aromatic:Artemisia maritime:Hedychium spicatum* ranges from 1 to 20:1 to 20:1 to 5:1 to 5:1 to 20;
    [b] homogenizing the mixture obtained in step [a] at temperature in the range of 15 to 25° C. for 1 to 3 hours to obtain the formulation; and
    [c] diluting the formulation as obtained in step [b] by adding a diluting agent up to 10000 times prior to use.

2. The process as claimed in claim 1, wherein the ratio of *Valeriana jatamansi:Tagetes minuta:Artemisia maritime: Hedychium spicatum* is 10:5:5:20.

3. The process as claimed in claim 1, wherein the ratio of *Valeriana jatamansi:Tagetes minuta:Artemisia maritime: Hedychium spicatum* is 20:10:5:10.

4. The process as claimed in claim 1, wherein the essential oils are obtained
    from the aerial parts or from rhizomes or a combination of both of aromatic crops selected from *Valeriana jatamansi, Tagetes minuta, Curcuma aromatic, Artemisia maritime*, and *Hedychium spicatum*.

5. The process as claimed in claim 1, wherein the essential oils are extracted using the method selected from the group consisting of solvent distillation, steam distillation, hydro distillation and hydro-steam distillation for a period in the range of 5 minutes to 96 hours.

6. The process as claimed in claim 1, wherein the diluting agent is selected from the group consisting of a non-polar solvent, a medium polar solvent, an organic solvent, an inorganic solvent, an emulsion, a commercial cream, a gel, and a lotion or combination thereof.

* * * * *